United States Patent [19]

Willis et al.

[11] 4,281,204

[45] Jul. 28, 1981

[54] SUBSTITUTED SPIROCYCLIC DERIVATIVES

[75] Inventors: Brian J. Willis, Bergenfield, N.J.; Robert G. Eilerman, Merrick, N.Y.

[73] Assignee: Fritzsche Dodge & Olcott Inc., New York, N.Y.

[21] Appl. No.: 82,066

[22] Filed: Oct. 5, 1979

[51] Int. Cl.³ .................... C07C 45/61; C07C 49/427
[52] U.S. Cl. .................... 568/361; 568/343; 568/345; 568/347; 568/349; 568/374
[58] Field of Search ............ 568/367, 374, 343, 347, 568/349, 345, 361

[56] References Cited

U.S. PATENT DOCUMENTS

4,203,925  5/1980  Barton et al. ................ 568/362

OTHER PUBLICATIONS

Stork et al., "J.A.C. Soc." (1973) 95, 3414.
Daub et al., "J.A.C. Soc." (1975) 97, 1622.
Marshall et al., "J. Org. Chem." (1970) 35, 192.
Buchi et al., "J. Org. Chem." (1976) 41, 3209.
Deighton et al., "J.C.S. Chem. Comm.", (1975) 662.
Bozzar et al., "J.C.S. Chem. Comm." (1974) 1005.
Caine et al., "Tetrahedron Lett.", (1974) 703.
Yamada et al., "Tetrahedron Lett." (1973) 4963.

*Primary Examiner*—Werren B. Lone
*Attorney, Agent, or Firm*—Cooper, Dunham, Clark, Griffin & Moran

[57] ABSTRACT

The present invention relates to substituted spirocyclic derivatives having the general formula:

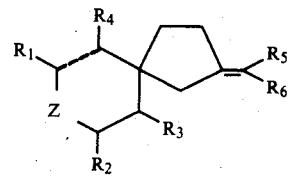

wherein the dotted line represents a carbon-carbon double bond or a carbon-carbon single bond, wherein $R_1$, $R_2$, $R_3$, $R_4$, $R_5$, and $R_6$ are each the same or different, hydrogen or lower alkyl, wherein Z is one of the following:

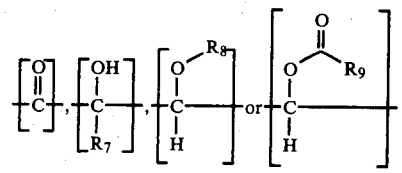

wherein $R_7$ is either hydrogen or lower alkyl, wherein $R_8$ and $R_9$ are each lower alkyl; their methods of preparation and their use as odor-modifying ingredients in perfumes and perfumed products, and as flavor-modifying ingredients in the flavoring of foodstuffs and tobacco products.

6 Claims, No Drawings

SUBSTITUTED SPIROCYCLIC DERIVATIVES

This application is related to an earlier application Ser. No. 914,160, filed on June 9, 1978 now U.S. Pat. No. 4,203,925, the disclosure of which is hereby incorporated by reference.

BACKGROUND OF THE INVENTION

There is an increased demand for materials which can be utilized to modify the flavor and/or fragrance of consumable items. The natural oils which have traditionally been used for this purpose often suffer the disadvantages of limited supply, high cost, and variable quality.

Accordingly, the search for synthetics which can function as partial or total replacements for essential oils, or which can find use in the creation of new and unique flavor and fragrance materials has intensified in recent years.

One specific example of a compound which can be prepared by the process of this invention is 2-isopropylidene-6,10-dimethylspiro[4.5]dec-6-en-8-one represented by the structure:

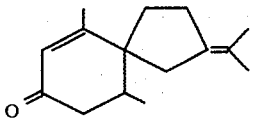

one epimer of which is commonly referred to as β-vetivone. It is a naturally occurring component of the oil obtained by steam distillation of the roots of Vetiveria zizanioides, and generally considered to be an important contributor to the overall odor character of the oil (Arctander, "Perfume and Flavor Chemicals," #3089, 1969).

Previous methods for the preparation of β-vetivone have been set forth by Marshall and Johnson, J. Org. Chem., 1970, 35, 192; Yamada, Nagase, Hayakawa, Aoki and Hirata, Tetrahedron Lett., 1973, 4963; Stork, Danheiser and Ganem, J. Amer. Chem. Soc., 1973, 95, 3414; McCurry, Singh and Link, Tetrahedron Lett., 1973, 1155; Caine and Chu, Tetrahedron Lett., 1974, 703; Bozzar, Bachmann and Pesaro, J.C.S. Chem. Commun., 1974, 1005; Dauben and Hart, J. Amer. Cham. Soc., 1975, 97, 1622; Deighton, Hughes and Ramage, J.C.S. Chem. Commun., 1975, 662, Buchi, Berthet, Decorzant, Gieder and Hauser, J. Org. Chem., 1976, 41, 3209 and McCurry and Singh, Tetrahedron Lett., 1973, 3325.

Related references include Coxon, Price and Chee, Tetrahedron Lett., 1974, 2921; Hikino, Aota, Kuwana, and Takemoto, Tetrahedron, 27, 4831 (1971); and German Pat. No. 2,353,147 (1974).

DETAILED DESCRIPTION OF THE INVENTION

It has been found that new and novel flavors and flavoring compositions, perfumes and perfumed articles, as well as tobacco products can be successfully produced by adding effective amounts of one or more of the substituted spirocyclic derivatives having the general formula:

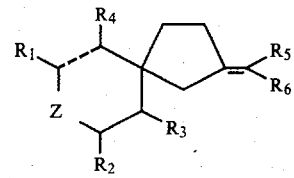

wherein the dotted line represents a carbon-carbon double bond or carbon-carbon single bond, wherein $R_1$, $R_2$, $R_3$, $R_4$, $R_5$ and $R_6$ are each the same or different hydrogen or lower alkyl, wherein Z is one of the following:

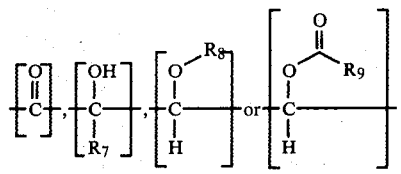

wherein $R_7$ is either hydrogen or lower alkyl, and wherein $R_8$ and $R_9$ are each lower alkyl.

The substituted spirocyclic compounds of the present invention have been found to possess distinctive balsamic, amber-like, woody, sweet, rooty, musty, earthy, leathery, green, citrus-like, herbaceous, floral odors which are useful in fine fragrances as well as perfumed products such as soaps, detergents, deodorants, cosmetic preparations and the like.

One or more of the substituted spirocyclic compounds of this invention and auxiliary perfume ingredients, for example, alcohols, aldehydes, ketones, nitriles, esters and essential oils, may be admixed so that the combined odors of the individual components produce a desired fragrance. Such perfume compositions are carefully balanced, harmonious blends of essential oils, aroma chemicals, resinoids and other extracts of natural odorous materials. Each ingredient imparts its own characteristic effect to the composition. Thus, one or more of the substituted spirocyclic compounds of the invention can be employed to impart novel characteristics into fragrance compositions.

Such compositions may contain up to about 80 weight percent of any one or more of the substituted spirocyclic compounds of this invention. Ordinarily, at least about 0.001 weight percent of the substituted spirocyclic compund is required to impart significant odor characteristics. Amounts in the range of from about 1 to about 60 weight percent are preferred. The substituted spirocyclic compounds of this invention may be formulated into concentrates containing from about 1 to about 60 weight percent of the chemical in an appropriate solvent. Such concentrates are then employed to formulate products such as colognes, soaps, etc., wherein the concentration of the chemicals of this invention can be in the range of from about 0.001 to about 7 weight percent, depending upon the final product. For example, the concentration of the chemicals of this invention will be of the order of about 0.001 to about 0.1 weight percent in detergents, and of the order of about 0.01 to about 7 weight percent in perfumes and colognes.

The substituted spirocyclic compounds of this invention are useful as olfactory components of perfume compositions for detergents and soaps, space odorants and deodorants; perfumes; colognes; toilet water; bath preparations such as bath oils and bath solids; hair preparations such as lacquers, brilliantines, pomades and shampoos; cosmetic preparations such as creams, deodorants, hand lotions and sunscreens; powders such as talcs, dusting powders and face powders; and the like.

Because of their unique organoleptic properties, the substituted spirocyclic compounds of this invention have also been found to have utility in the alteration of the flavor component or components of flavor compositions. They can be used effectively to impart a certain natural character to artificial flavors. They can also be employed successfully to modify the organoleptic properties of such consumables as chewing gum, beverages, pharmaceutical preparations, fruit juices and the like.

The flavoring properties of the substituted spirocyclic compounds of this invention depend upon the type of products to which they are added. They develop woody, earthy, minty, fruity, citrus-like flavor notes or combinations thereof. They can be employed advantageously in certain citrus products such as orange oil to round off the taste and in grape flavors where the taste and aroma are markedly enhanced.

Again the proportions of the substituted spirocyclic compounds of this invention can vary within a wide range of concentrations depending upon the organoleptic properties desired. Typically, particularly interesting flavor effects can be obtained with concentrations of 0.001 to 1 weight percent of the compound in the final flavor composition. In some situations, higher concentrations of the substituted spirocyclic compounds are required to produce special flavoring effects. For example, when used in artificial flavor compositions, they may be incorporated at levels of 20 weight percent, or even more.

When one or more of the substituted spirocyclic compounds of this invention is added to smoking tobacco, or synthetic tobacco, they impart woody, amber-like, and cedarwood notes to the tobacco aroma. The proportions are preferably between 1 to 100 ppm, but in certain situations higher levels may be usefully employed.

The description of the practice of the instant invention set forth above is meant to illustrate its usefulness and is in no way designed to limit the scope of the invention.

In accordance with one of the embodiments of the present invention, the compounds of the invention can be prepared by one of several processes. In one of the processes outlined hereinbelow the starting material is an appropriately substituted 2,4-dioxocyclohexane carboxylate having the general formula:

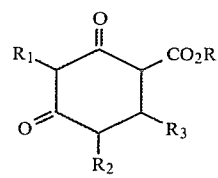

(I)

wherein $R_1$, $R_2$, and $R_3$ are as defined above, and R is methyl or ethyl, preferably methyl. Specific examples of carboxylates (I) falling within the scope of the foregoing structural formula include the following:

Methyl 2,4-dioxo-3-methylcyclohexane carboxylate
Methyl 2,4-dioxo-5-methylcyclohexane carboxylate
Methyl 2,4-dioxo-6-methylcyclohexane carboxylate
Methyl 2,4-dioxo-3,5-dimethylcyclohexane carboxylate
Methyl 2,4-dioxo-3,6-dimethylcyclohexane carboxylate
Methyl 2,4-dioxo-5,6-dimethylcyclohexane carboxylate
Methyl 2,4-dioxo-3,5,6-trimethylcyclohexane carboxylate
Methyl 2,4-dioxo-3-methyl-5-ethylcyclohexane carboxylate
Methyl 2,4-dioxo-3-methyl-6-ethylcyclohexane carboxylate
Methyl 2,4-dioxo-3-methyl-5,6-ethylcyclohexane carboxylate
Methyl 2,4-dioxo-5-methyl-3-ethylcyclohexane carboxylate
Methyl 2,4-dioxo-5-methyl-6-ethylcyclohexane carboxylate
Methyl 2,4-dioxo-5-methyl-3,6-diethylcyclohexane carboxylate
Methyl 2,4-dioxo-6-methyl-3-ethylcyclohexane carboxylate
Methyl 2,4-dioxo-6-methyl-5-ethylcyclohexane carboxylate
Methyl 2,4-dioxo-6-methyl-3,5-diethylcyclohexane carboxylate
Methyl 2,4-dioxo-3,5,6-triethylcyclohexane carboxylate
Methyl 2,4-dioxo-3-methyl-5-propylcyclohexane carboxylate
Methyl 2,4-dioxo-3-methyl-6-propylcyclohexane carboxylate
Methyl 2,4-dioxo-3-methyl-5,6-dipropylcyclohexane carboxylate
Methyl 2,4-dioxo-5-methyl-3-propylcyclohexane carboxylate
Methyl 2,4-dioxo-5-methyl-6-propylcyclohexane carboxylate
Methyl 2,4-dioxo-6-methyl-3,6-dipropylcyclohexane carboxylate
Methyl 2,4-dioxo-6-methyl-3-propylcyclohexane carboxylate
Methyl 2,4-dioxo-6-methyl-5-propylcyclohexane carboxylate
Methyl 2,4-dioxo-6-methyl-3,5-dipropylcyclohexane carboxylate
Methyl 2,4-dioxo-3,5,6-tripropylcyclohexane carboxylate
Methyl 2,4-dioxo-3-methyl-5-isopropylcyclohexane carboxylate
Methyl 2,4-dioxo-3-methyl-6-isopropylcyclohexane carboxylate
Methyl 2,4-dioxo-3-methyl-5,6-diisopropylcyclohexane carboxylate
Methyl 2,4-dioxo-5-methyl-3-isopropylcyclohexane carboxylate
Methyl 2,4-dioxo-5-methyl-6-isopropylcyclohexane carboxylate
Methyl 2,4-dioxo-5-methyl-3,6-diisopropylcyclohexane carboxylate
Methyl 2,4-dioxo-6-methyl-3-isopropylcyclohexane carboxylate
Methyl 2,4-dioxo-6-methyl-5-isopropylcyclohexane carboxylate
Methyl 2,4-dioxo-6-methyl-3,5-diisopropylcyclohexane carboxylate
Methyl 2,4-dioxo-3,5,6-triisopropylcyclohexane carboxylate
Methyl 2,4-dioxo-3-ethylcyclohexane carboxylate
Methyl 2,4-dioxo-5-ethylcyclohexane carboxylate
Methyl 2,4-dioxo-6-ethylcyclohexane carboxylate
Methyl 2,4-dioxo-3-ethyl-5-propylcyclohexane carboxylate Methyl 2,4-dioxo-3-ethyl-6-propylcyclohexane carboxylate
Methyl 2,4-dioxo-3-ethyl-5,6-dipropylcyclohexane carboxylate
Methyl 2,4-dioxo-5-ethyl-3-propylcyclohexane carboxylate
Methyl 2,4-dioxo-5-ethyl-6-propylcyclohexane carboxylate
Methyl 2,4-dioxo-5-ethyl-3,6-dipropylcyclohexane carboxylate
Methyl 2,4-dioxo-6-ethyl-3-propylcyclohexane carboxylate
Methyl 2,4-dioxo-6-ethyl-5-propylcyclohexane carboxylate
Methyl 2,4-dioxo-6-ethyl-3,5-dipropylcyclohexane carboxylate
Methyl 2,4-dioxo-3-propylcyclohexane carboxylate
Methyl 2,4-dioxo-5-propylcyclohexane carboxylate
Methyl 2,4-dioxo-6-propylcyclohexane carboxylate
Methyl 2,4-dioxo-3-propyl-5-isopropylcyclohexane carboxylate
Methyl 2,4-dioxo-3-propyl-6-isopropylcyclohexane carboxylate
Methyl 2,4-dioxo-3-propyl-5,6-diisopropylcyclohexane carboxylate
Methyl 2,4-dioxo-5-propyl-3-isopropylcyclohexane carboxylate
Methyl 2,4-dioxo-5-propyl-6-isopropylcyclohexane carboxylate
Methyl 2,4-dioxo-5-propyl-3,6-diisopropylcyclohexane carboxylate
Methyl 2,4-dioxo-6-propyl-3-isopropylcyclohexane carboxylate
Methyl 2,4-dioxo-6-propyl-5-isopropylcyclohexane carboxylate
Methyl 2,4-dioxo-6-propyl-3,5-diisopropylcyclohexane carboxylate Some of these are known compounds and to the extent that they are new, known methods such as those diagrammed in Scheme A can be employed for their production.

Scheme A

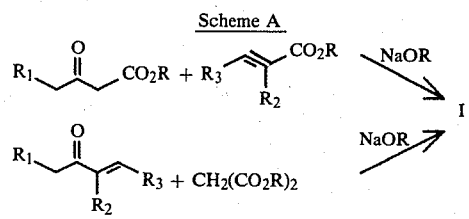

PROCESS 1

The appropriate 2,4-dioxocyclohexane carboxylate (I) is subjected to enol ether formation by treatment with a lower alkanol, preferably isopropanol or isobutanol, in the presence of an acidic catalyst. The reaction may be successfully carried out with a mineral acid or with p-toluenesulfonic acid in a hydrocarbon solvent, for example, an aromatic solvent, such as benzene, toluene, xylene and the like, and with azeotropic removal of water (as disclosed in German Pat. No. 2,335,080). The reaction results in a compound with substantially the structure:

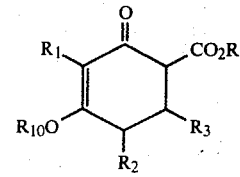

wherein $R_{10}$ is lower alkyl, preferably isopropyl or isobutyl.

The carboxylate II is then alkylated. The alkylation may be carried out in the presence of an alkali metal hydride, such as sodium hydride or potassium hydride, with a 2-alkylidene-1,4-disubstituted butane having the structure:

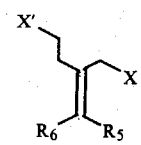

wherein X and X' are halogens chloro, bromo, or iodo, preferable chloro, and $R_5$ and $R_6$ are the same or different hydrogen or lower alkyl. The reaction is carried out in any suitable solvent, for example, benzene, toluene, xylene, hexane, dimethyl sulfoxide, dimethylformamide, hexamethylphosphoric triamide, tetrahydrofuran, or dimethoxyethane. Temperatures in the range of 0° to 120° C. may be employed with the temperature range of 20° to 80° C. being preferred. Although either compound may be used in excess, the preferred molar ratio of olefinic dihalide to carboxylate is from 1:1 up to 1.2:1. Reaction times of from 1 to 15 hours are required depending upon the temperature and solvent utilized. The resulting carboxylate has the structure:

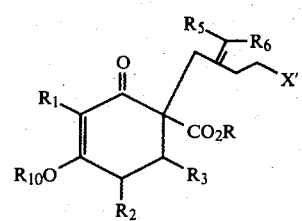

Alternatively, the alkylation may be carried out in the presence of a phase transfer catalyst. Specific examples of phase transfer catalysts useful in the present invention include benzyltriethylammonium chloride, cetyltrimethylammonium chloride and tricaprylmethylammonium chloride. The alkylation of carboxylate II with the olefinic dihalide may be successfully carried out in the presence of approximately one equivalent of a base such as an alkali or alkaline earth metal alkoxide, alkali metal hydride, hydroxide or carbonate in an inert solvent such as benzene, toluene, xylene, hexane, dimethylformamide, or methylene chloride. Temperatures in the range of about 20° to 150° C. may be employed, the temperature range of 30° to 100° C. being preferred. The amount of phase transfer catalyst based on carboxylate II may vary from 0.1 to 10 mole percent, the preferred amount being in the range 0.5 to 5 mole percent.

Spiroannulation of carboxylate III is accomplished by decarboxylative alkylation. Carboxylate III undergoes a novel intramolecular decarboxylative alkylation by heating it in the presence of an alkali metal salt in a polar aprotic solvent such as dimethylsulfoxide, dimethylformamide, hexamethylphosphoric triamide or 2-methylpyrrolidone, resulting in production of the spiroketone having the structure:

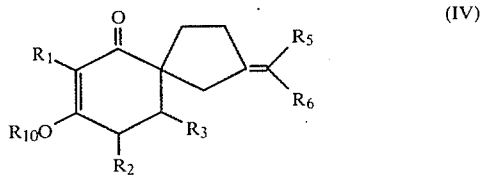

wherein the substituents are as set forth above. Preferred metal salts include lithium chloride, lithium bromide, lithium iodide, sodium chloride, sodium iodide, and sodium cyanide. The reaction is desirably carried out at temperatures of 80° to 160° C. with temperatures in the range of 100° to 140° C. being preferred. The mole ratio of carboxylate to alkali metal salt may be from 1:0.5 to 1:10, preferably from 1:1.5 up to 1:2.

Conversion of the spiroketone intermediate IV to the compounds of the instant invention may be accomplished by any one or a combination of the steps outlined hereinbelow (see Scheme B). For example, IV may be reacted with an organometallic derivative such as a Grignard reagent (e.g. $R_4MgX$) or an organolithium compound (e.g. $R_4Li$) wherein $R_4$ is lower alkyl. The reaction with the organometallic is desirably carried out with a stoichiometric quantity of the reagent when the lithium derivative is utilized or with excess organometallic (2 to 3 equivalents) when a Grignard reagent is employed. The reaction is preferably carried out in an inert solvent such as diethyl ether, tetrahydrofuran, or mixtures of diethyl ether or tetrahydrofuran in benzene, toluene or hexane. It is preferred to carry out the reaction in an inert atmosphere such as nitrogen or argon and at temperatures in the range of from 0° to 50° C. The resulting organometallic adduct is then hydrolyzed with a dilute aqueous mineral acid such as hydrochloric acid. The hydrolyzed product may be isolated by solvent extraction and purified by fractional distillation or crystallization to give the substituted spiroketone V. This ketone may be utilized in perfume or flavor compositions or further modified.

The spiroketone V may be treated with a Grignard reagent $R_7MgX$ such as $CH_3MgI$ or an organolithium, $R_7Li$, wherein $R_7$ is lower alkyl under reaction conditions essentially the same as those stated hereinabove. In this instance, the hydrolysis is desirably accomplished with either ice-cold aqueous mineral acid or, more preferably, with a saturated ammonium chloride solution resulting in a compound having the structure IX.

Reduction of the spiroketone V may be carried out, for example, with hydrogen gas in the presence of a catalyst such as 5% palladium or carbon, Raney nickel, or copper chromite in a solvent such as a lower alkanol or hydrocarbon such as hexane.

The reaction may be carried out in a Parr reaction vessel at elevated pressures, for example, at 1–5 atmospheres, and at elevated temperatures, for example, from 20° to 100° C. This results in compounds VII or VIII depending upon the conditions employed. Alternatively, compound VII may be reduced using standard methodology, for example, by means of an alkali metal aluminum hydride such as lithium aluminum hydride in an inert solvent such as diethyl ether or tetrahydrofuran at temperatures of from 0° to 50° C. Likewise, a boron hydride such as sodium borohydride in a lower alkanol may be employed resulting in the preparation of compound VIII. Either of these materials may be utilized in perfume or flavor compositions.

Reduction of the ketone group in V may also be effected with an alkali metal aluminum hydride such as diisobutylaluminum hydride or lithium aluminum hydride in an inert solvent followed by hydrolysis to give the corresponding alcohol VI which may be utilized in perfume or flavor compositions. This reaction is preferably carried out at temperatures in the range from about 0° to 50° C.

Spiroketone VII may be reacted with an organometallic such as a Grignard reagent (e.g. $R_7MgX$) or an organolithium $R_7Li$ wherein $R_7$ is lower alkyl under conditions similar to those described above for ketone V thus leading to formation of the alcohol X which itself may be utilized in perfume or flavor compositions.

SCHEME B

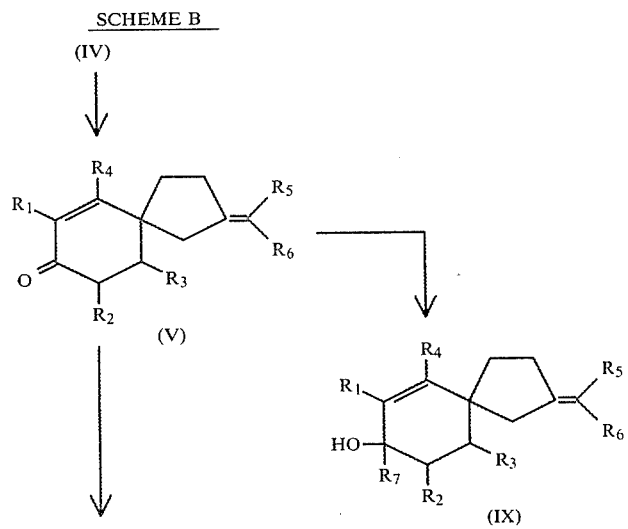

-continued
SCHEME B

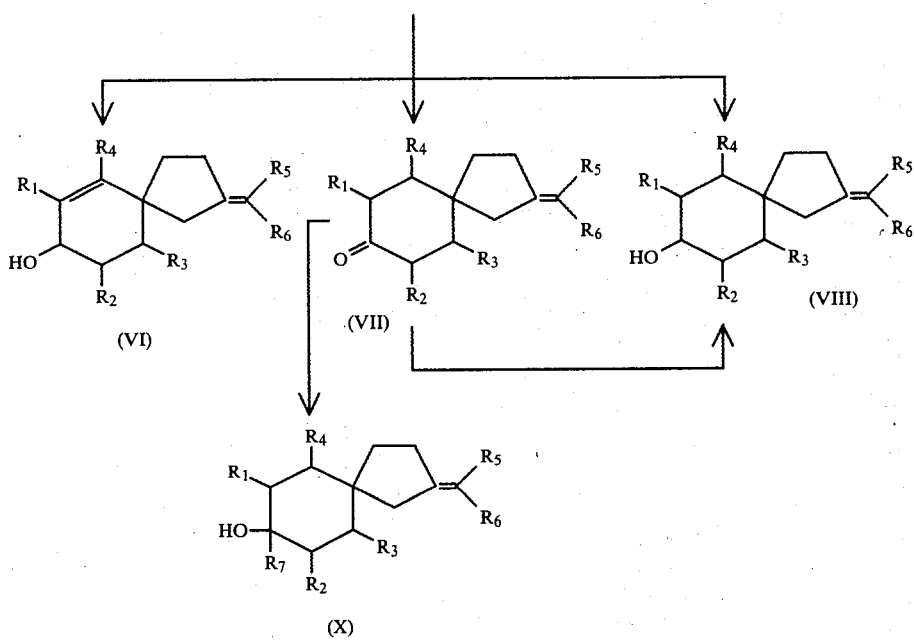

(VI) (VII) (VIII)

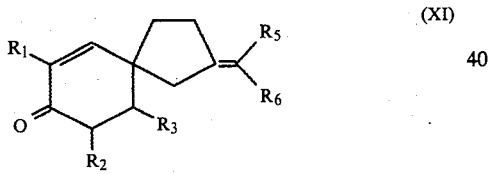

(X)

In accordance with another embodiment of the present invention, the ketone group in IV may be reduced with an alkali aluminum hydride such as lithium aluminum hydride in an inert solvent such as tetrahydrofuran or diethyl ether. Temperatures of from 0° to 50° C. may be used. Hydrolytic work-up employing a dilute mineral acid such as hydrochloric acid, results in the formation of the ketone having the structure:

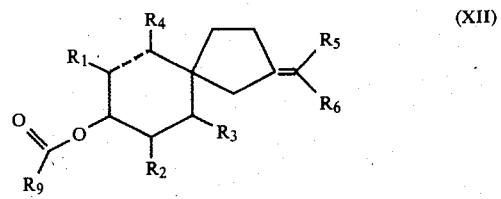

(XI)

This ketone may be utilized in perfume and flavor compositions or further modified by the same techniques described hereinabove for the compounds illustrated in Scheme B wherein $R_4$ is now equal to hydrogen.

In addition, the spiroketone XI may be reacted with an organometallic reagent such as $(R_4)_2LiCu$ or a Grignard reagent $R_4MgX$ in the presence of a catalytic amount of a copper salt, i.e. cuprous iodide, wherein $R_4$ is lower alkyl according to known methods (see, for example, G. Posner in "Organic Reactions", Vol. 19, p1, 1972). Temperatures in the range of from −30° C. up to 20° C. are typically employed and the solvent may be, for example, tetrahydrofuran or diethyl ether. Reactions times of from 1 to 10 hours are required and hydrolysis using an aqueous mineral acid results in a compound having the formula VII.

The spiro alcohols VI and VIII may, in addition, be subjected to esterification in accordance with standard techniques (see L. F. Fieser & M. Fieser, "Reagents for Organic Synthesis", Vol. I, p. 958, 1967). For example, esterification with an alkanoic acid anhydride such as acetic anhydride or propionic anhydride or treatment with an acyl halide, preferably an acyl chloride in the presence of an organic base such as N,N-dimethylaniline to form compounds having the structure:

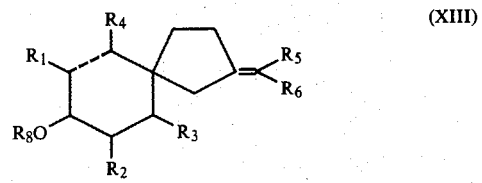

(XII)

wherein $R_9$ is lower alkyl and the dotted line represents a carbon-carbon double bond or a carbon-carbon single bond.

In accordance with a further embodiment of the present invention, the alcohol group in both compound VI and compound VIII may be converted by etherification to compounds having the structure:

(XIII)

wherein $R_8$ is lower alkyl and the dotted line represents either a carbon-carbon double bond or a carbon-carbon single bond. The transformation may be effected by known techniques (see J. March, "Advanced Organic Chemistry", 2nd ed., p. 357 (1977)). For example, the alcohol may be treated with an alkali metal hydride such as sodium hydride in an inert solvent followed by alkylation of the resulting alkoxide with either an alkyl halide $R_8X$ (e.g. $CH_3I$) or an alkyl sulfate $(R_8)_2SO_4$ (e.g. $(CH_3)_2SO_4$) to generate the compounds of formula XIII.

PROCESS 2

A phenol having the structure:

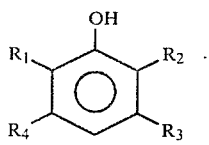 (XIV)

wherein $R_1$, $R_2$, $R_3$, and $R_4$ are the same or different hydrogen or lower alkyl may be reacted with a 2-alkylidene-1, 4-disubstituted butane having the structure:

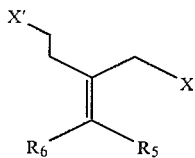

wherein $R_5$ and $R_6$ are the same or different hydrogen or lower alkyl and wherein the symbols X and X' are selected from leaving groups such as halogen, preferably chlorine, and sulfonate of the structure —O—SO$_2$R wherein R may be an aliphatic or aromatic hydrocarbon radical such as methyl or p-tolyl. Alternatively, X and X' together may form a cyclic sulfate group, e.g.

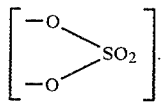

In most cases it is preferred that X equal X'.

Specific examples of phenols (XIV) falling within the scope of the foregoing structural formula include the following:
3,5-dimethylphenol
3,5-diethylphenol
3,5-dipropylphenol
2,3,5-trimethylphenol
2,3,5-triethylphenol
2,3,5-tripropylphenol
2,3,5,6-tetramethylphenol
2,3,5,6-tetraethylphenol
2,3,5,6-tetrapropylphenol
2,6-diethyl-3,5-dimethylphenol
2,6-dipropyl-3,5-dimethylphenol
2,6-dimethyl-3,5-diethylphenol
2,6-dimethyl-3,5-dipropylphenol
2,3-dimethyl-5,6-diethylphenol
2,3-dimethyl-5,6-dipropylphenol
2,3-diethyl-5,6-dipropylphenol
2,5-dimethyl-3,6-diethylphenol
2,5-dimethyl-3,6-dipropylphenol
2,5-diethyl-3,6-dipropylphenol Specific examples of 2-alkylidene-1,4-disubstituted butanes falling within the scope of the foregoing formula are 2-(2'-propylidene)-1,4-dichlorobutane, 2-(2'-butylidene)-1,4-dibromobutane, 2-(2'pentylidene)-1,4-bis (para-toluene sulfonyl) butane and

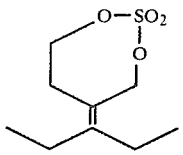

The alkylation is effected by reacting the phenol with the olefinic compound at a temperature in the range of from about −70° to 140° C., preferably in the range of from about −30° to 110° C. in the presence of a base. Short reaction times, lower reaction temperatures, and weaker bases favor formation of an intermediate having the structure:

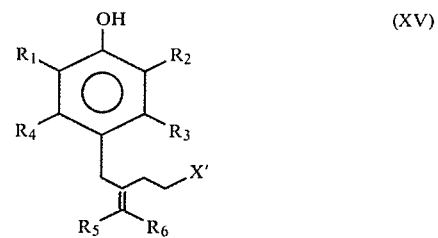 (XV)

which may be isolated by standard methods. This intermediate XV may then be converted in the presence of a base, either the same as or different from the base present during the initial alkylation, and at a temperature in the range of from about −70° to 220° C., to a spirodienone having the structure:

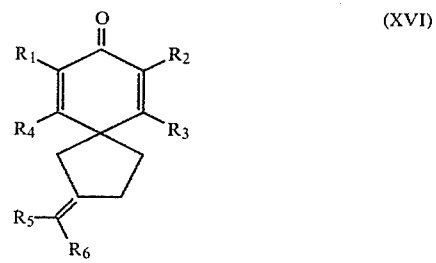 (XVI)

wherein $R_1$, $R_2$, $R_3$, $R_4$, $R_5$, and $R_6$ are as previously described.

If the spirodienone is volatile, the spiroannulation is conveniently carried out in a high boiling solvent, or in the absence of a solvent at a temperature of from about 140° to 220° C. under a partial vacuum, such that compound XVI distills from the reaction vessel as it is formed. Alternatively, the product may be isolated and purified by conventional techniques.

It is also possible to accomplish both the alkylation and spiroannulation steps without isolation of intermediate XV. Compounds XIV and the 2-alkylidene-1,4-disubstituted butane are reacted at a temperature in the range from about −70° to +220° C. in the presence of a base. Longer reaction times, high reaction temperatures, and stronger bases favor formation of the spirodienone XVI directly.

As in the case where intermediate XV is isolated and converted to spirodienone XVI, the reaction may be carried out in a high boiling solvent, or in the absence of solvent, if the spirodienone is volatile. Compound XVI may then be vacuum distilled from the reaction vessel at the end of the reaction. Alternatively, the product XVI may be isolated and purified by conventional techniques.

A wide variety of bases are useful for this reaction including: alkali metal hydroxides such as sodium and potassium hydroxide, as well as alkaline earth metal hydroxides such as calcium and barium hydroxide; alkali metal and alkaline earth metal salts such as carbonates, acetates, borates (e.g. sodium carbonate and sodium acetate); alkali metal and alkaline earth metal alkoxides such as potassium t-butoxide, sodium ethoxide, and magnesium methoxide; metal hydrides such as sodium hydride; organic bases including primary, secondary and tertiary amines such as monomethylamine, diethylamine and tributylamine, polyamines such as ethylene diamine, heterocyclic amines such as morpholine and pyridine, and alkanolamines such as diethanolamine. Ammonia and inorganic ammonium salts that hydrolyze to form ammonia in the presence of metal hydroxides such as ammonium chloride are effective. Also, ion exchange resins may be employed.

These reactions may be carried out in aqueous or non-aqueous solvent systems in the absence of a solvent. Thus, useful solvent systems include water, ethyl alcohol, dimethylformamide, tetrahydrofuran, hexane, toluene, tetralin, mineral oil, dibutylphthalate, and mixed solvent systems such as water/ethyl alcohol, water/tetrahydrofuran, and toluene/dimethylformamide. Further, these reactions may advantageously be catalyzed by metal salts such as copper sulfate, copper chloride, copper oxide, ferrous sulfate and cobalt chloride.

Conversion of the spirodienone to compounds mentioned in Process 1 may be accomplished by the sequence illustrated in Scheme C. For example, selective reduction in the presence of a hydrogenation catalyst such as 5% palladium on carbon in an inert solvent such as ethanol or hexane with one equivalent of hydrogen gas at atmospheric pressure results in a compound having the structure:

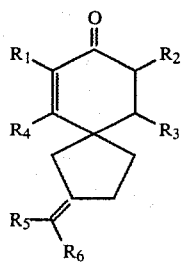

(V)

which may be utilized in perfume or flavor compositions.

Alternatively, reduction with hydrogen gas in the presence of a metal catalyst such as palladium, platinum, or Raney nickel at temperatures of from 20° to 50° C. and at pressures of from 1 to 10 atmospheres results in reduction of both the ring olefinic bonds of the spirodienone resulting in a compound having the structure:

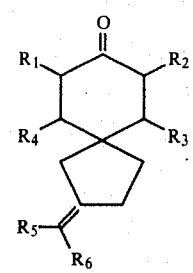

(VII)

which may be utilized in perfume or flavor compositions or further reacted under conditions essentially the same as those described under the previous processes to generate compounds VI and VIII.

SCHEME C

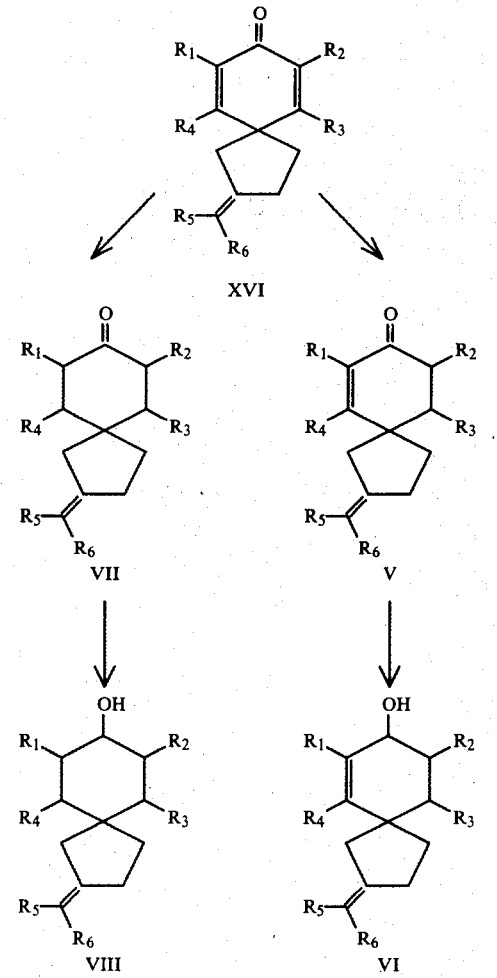

Examples of spirocyclic compounds which have been prepared according to the foregoing process include: 2-isopropylidene-6,10-dimethylspiro[4.5]dec-6-en-8-one, 2-isopropylidene-7,9-dimethylspiro[4.5]decan-8-one, 2-isobutylidene-6,10-dimethylspiro[4.5]dec-6-en-8-one, and 2-isopropylidene-7,9-dimethylspiro[4.5]dec-6-en-8-one. All of these have been found to possess particularly desirable fragrance and fixative properties.

Isolation and purification of the final products of the present invention is achieved by conventional techniques which include extraction, distillation, crystallization, preparative chromatographic separation and the like.

It will be recognized that the compounds of the present invention can exist in several stereoisomeric forms, including the "R" and "S", as well as the "cis" and "trans" isomers. The foregoing structural formulae are intended to embrace the individual steroisomers as well as mixtures of the various stereoisomers of the substituted spirocyclics of this invention.

The following examples are set forth to more fully illustrate the practices of this invention, but are in no way meant to limit the scope thereof.

EXAMPLE 1

Methyl 2-oxo-4-isopropoxy-6-methyl-3-cyclohexene carboxylate

A mixture of methyl 2,4-dioxo-6-methylcyclohexane carboxylate (184 g, 1 mol), isopropanol (96 g, 1.6 mol) and p-toluenesulfonic acid (2 g) in benzene (600 mL) was heated at reflux for 6 hours with azeotropic removal of water. After cooling, the solution was washed several times with 5% sodium carbonate solution and the benzene then removed on a rotary evaporator. Short path distillation gave 171.6 g of the carboxylate, bp 110°–112° C./0.05 mm.

IR (film): 1750, 1665, 1610 cm$^{-1}$

NMR (CDCl$_3$): 1.08(3H,d,J=5.5 Hz), 1.32(6H,d,J=6 Hz), 2.0–2.9(3H,m), 3.1(1H,dd), 3.8(3H,s), 4.5(1H,h,J=6 Hz), 5.42(1H,bs) δ.

EXAMPLE 2

2-isopropylidene-8-isopropoxy-10-methylspiro[4.5]dec-7-en-6-one

Reaction A:

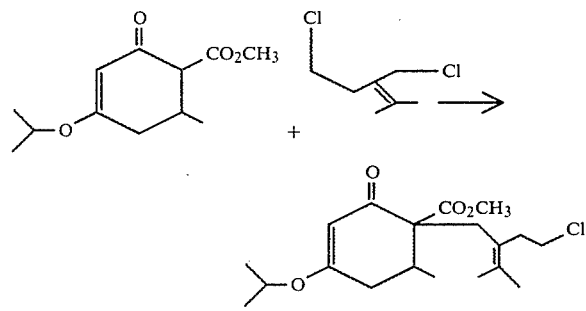

Reaction B:

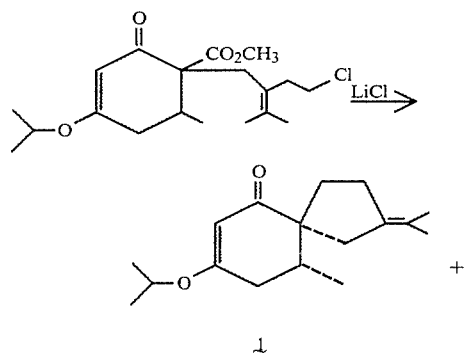

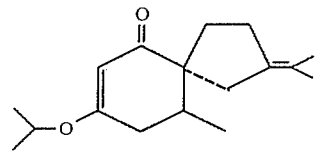

Reaction A:

To a slurry of mineral oil-free sodium hydride (5.8 g, 0.24 mol) in dry dimethylformamide (160 mL) under nitrogen was added a solution of methyl 2-oxo-4-isopropoxy-6-methyl-3-cyclohexene carboxylate (49 g, 0.22 mol), prepared according to Example 1, in dimethylformamide (80 mL) over a period of 40 minutes. The mixture was stirred at 35° C. for an additional 30 minutes. A solution of 2 isopropylidene-1,4-dichlorobutane (40.1 g), 0.24 mol; see J. Amer. Chem. Soc. 1973, 95, 3414) in an equal volume of dimethylformamide was added over 1 hour with periodic cooling so that the temperature did not exceed 40° C. Stirring was continued for 3 hours at room temperature and then methanol (5 mL) was added. The reaction mixture was poured into water (2000 mL) and extracted with ether. The combined extracts were washed with water, brine, and dried (Na$_2$SO$_4$). Evaporation of the solvent under reduced pressure gave 75 g of crude material which was crystallized from pentane to yield 66.5 g of methyl 1-(2-isopropylidene-4-chlorobutyl)-2-oxo-4-isopropoxy-6-methyl-3-cyclohexene carboxylate, mp 76°–77° C.

IR (CHCl$_3$): 1740, 1638, 1610 cm$^{-1}$

NMR (CDCl$_3$): 0.95(3H,d), 1.31(6H,d,J=6 Hz), 1.75(6H,2s), 1.8–2.9(5H,m), 3.03(2H,bs), 3.45(2H,t), 3.65(3H,s), 4.5(1H,h,J=6 Hz), 5.5(1H,bs) δ.

Reaction B

Dry lithium chloride (3.8 g, 0.09 mol) and methyl 1-(2-isopropylidene-4-chlorobutyl)-2-oxo-4-isopropoxy-6-methyl-3-cyclohexene carboxylate (21.3 g, 0.06 mol) were mixed in anhydrous hexamethylphosphoric triamide (120 mL) under nitrogen. The solution was heated at 130° C. for 40 minutes and after cooling was poured into water (300 mL). The mixture was extracted with ether and the extract dried (Na$_2$SO$_4$). Solvent removal gave 15.2 g of crude spiroketones 1 and 2 (glc purity of 93%, spiroketones separated on HPLC). Crystallization from petroleum ether gave 12.9 g of 2-isopropylidene-8-isopropoxy-10-methylspiro[4.5]dec-7-en-6-one isomer 1 exclusively, mp 77°–77.5° C.

IR(CHCl$_3$): 1650, 1615 cm$^{-1}$

NMR(CDCl$_3$): 1.0(3H,d), 1.3(6H,d,J=6 Hz), 1.62(6H,bs), 1.8–2.9(9H,m), 4.45(1H,h,J=6 Hz), 5.25(1H,s) δ.

MS: 262 (M+), 136, 203, 69, 177, 138

EXAMPLE 3

2-isopropylidene-10-methylspiro [4.5]-dec-6-en-8-one

To a stirred suspension of lithium aluminum hydride (0.15 g, 4 mmol) in anhydrous ether (10 ml) was added 2-isopropylidene-8-isopropoxy-10-methylspiro[4.5]dec-7-en-6-one (2 g, 8 mmol), prepared according to Example 2. The mixture was heated at reflux for 1 hour and water cautiously added. The solution was mixed with 10% hydrochloric acid (30 mL) and agitated at room temperature for 45 minutes. The aqueous mixture was extracted with ether and the ether extracts washed with saturated sodium bicarbonate solution and dried (Na₂SO₄). The solution was concentrated and the crude ketone kugelrohr distilled to give 1.4 g, bp 130°/0.5 mm, of enone having the structure:

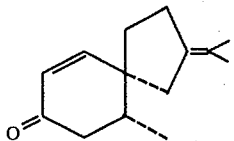

IR(film): 1680 cm⁻¹
NMR(CDCl₃): 1.0(3H,d), 1.62(6H,2s), 1.7–2.6(9H,m), 5.9(1H,d,J=10 Hz), 6.75(1H,d,J=10 Hz) δ. MS: 204 (M+), 122, 83, 91, 147, 67

EXAMPLE 4

2-isopropylidene-6,10-dimethylspiro[4.5]dec-6-en-8-one (β-vetivone)

To a solution of 2-isopropylidene-8-isopropoxy-10-methylspiro[4.5]dec-7-en-6-one (3.75 g, 0.015 mol), prepared according to Example 2, in anhydrous ether (50 mL) at 0° C. was added ethereal methyllithium (13.1 mL, 0.021 mol) over a period of 10 minutes. The mixture was allowed to slowly warm to room temperature and stirred for 3 hours. The solution was then cautiously added to 2 N hydrochloric acid (150 mL) and stirred at room temperature for 1.5 hours. The organic layer was separated and the aqueous solution extracted with ether. The ether extracts were combined, washed with brine, and dried (Na₂SO₄). Solvent removal and subsequent kugelrohr distillation gave 3 g of colorless oil which crystallized on standing. Recrystallization from hexane gave 2.9 g, mp 49.5°–50° C. of β-vetivone having the structure:

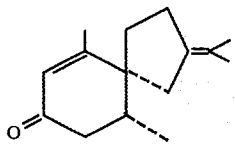

Glc/ms analysis demonstrates the absence of any epi isomer.
IR(CHCl₃): 1660, 1615 cm⁻¹
NMR(CDCl₃): 0.98(3H,d, 1.65(6H,bs), 1.8–2.65(12H, m with d at 1.9), 5.85(1H bs) δ.
MS: 218(M+), 136, 77, 67, 86, 121

EXAMPLE 5

2-isopropylidene-6-ethyl-10-methylspiro[4.5]dec-6-en-8-one

A Grignard solution was prepared from magnesium (1.17 g, 0.048 g-atom) and ethyl bromide (5.2 g, 0.048 mol) in anhydrous ether (50 mL) under nitrogen. 2-Isopropylidene-8-isopropoxy-10-methylspiro[4.5]dec-7-en-6-one (4 g, 0.015 mol), prepared according to Example 2, in anhydrous ether (20 mL) was added dropwise at room temperature and the mixture then heated at reflux for 4 hours. The solution was cautiously added to 2 N hydrochloric acid (200 mL) and stirred for 1 hour at room temperature. The mixture was extracted with ether and the ether extracts washed with saturated sodium bicarbonate, brine, and dried (Na₂SO₄). Kugelrohr distillation afforded 2.9 g, bp 165° C./0.5 mm, of enone having the structure:

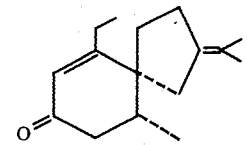

IR (film): 1670, 1625 cm⁻¹
NMR(CDCl₃): 0.95 and 1.05(6H,overlapping d and t), 1.65(6H,bs), 1.8–2.75(11H,m), 5.8(1H,bs) δ.
MS: 232(M+), 91, 66, 79, 105, 41

EXAMPLE 6

2-isobutylidene-10-methylspiro[4.5]dec-6-en-8one

Methyl 2-oxo-4-isopropoxy-6-methyl-3-cyclohexene carboxylate was reacted with 2-isobutylidene-1,4-dichlorobutane and the resultant alkylated carboxylate cyclized by the same method described in Example 2 to yield 2-isobutylidene-8-isopropoxy-10-methylspiro[4.5]dec-7-en-6-one having the structure:

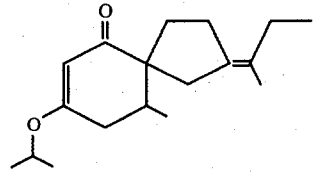

which was crystallized from petroleum ether, mp 88°–91° C.
IR(CHCl₃): 1650 1615 cm⁻¹
NMR(CDCl₃): 0.95(6H, m with superimposed d), 1.25(6H,d,J=6 Hz), 1.5–2.8(14H,m), 4.45(1H,h,J=6 Hz), 5.2(1H,s) δ.
MS: 276(M+), 139, 150, 138, 121, 69

To a stirred suspension of lithium aluminum hydride (0.19 g, 5 mmol) in anhydrous ether (15 mL) was added the 2-isobutylidene-8-isopropoxy-10-methylspiro[4.5]dec-7-en-6-one (2.7 g, 0.01 mol) in ether (3 mL). The mixture was heated at reflux for 1.5 hours followed by addition of wet ether. The resultant suspension was mixed with 10% hydrochloric acid (40 mL) and agitated at room temperature for 1 hour. The aqueous mixture was extracted with ether and the ether extracts washed with saturated sodium bicarbonate solution and dried (Na₂SO₄). The solution was concentrated and the crude ketone kugelrohr distilled to give 1.75 g, bp 135° C./0.5 mm, of the title enone having the structure:

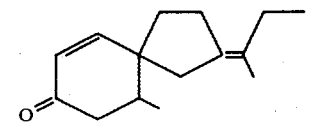

IR (film): 1680 cm⁻¹
NMR(CDCl₃): 1.0(6H,m), 1.5–2.6(14H,m), 5.75(1H,d,J=10 Hz), 6.6(1H,d,J=10 Hz) δ.
MS: 218(M+), 122, 97, 81, 91, 147

EXAMPLE 7

2-isopropylidene-6,10-dimethylspiro[4.5]decan-8-one

Reaction:

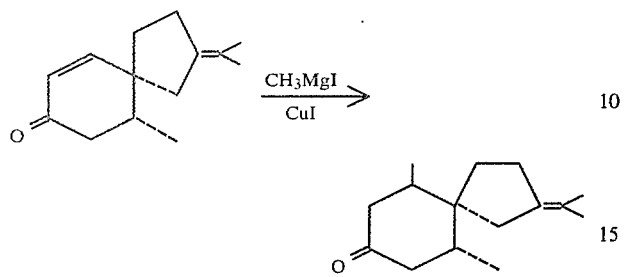

Cuprous iodide (0.25 g, 0.0013 mol) was added at −5° C. to a Grignard solution prepared from magnesium (0.61 g, 0.025 g-atom) and methyl iodide (3.6 g, 0.025 mol) in anhydrous ether (20 mL) under nitrogen. The mixture was stirred for 20 minutes and then 2-isopropylidene-10-methylspiro[4.5]dec-6-en-8-one (2 g, 0.01 mol), prepared according to Example 3, in ether (10 mL) was added dropwise. The mixture was stirred at 0° C. for 2.5 hours and then quenched with saturated NH4Cl solution (150 mL) which was made slightly basic by addition of NH4OH. The aqueous solution was extracted with ether and the combined extracts washed with water and dried (Na2SO4). Solvent removal and kugelrohr distillation gave 1.5 g of ketone, bp 130°–135° C./0.4 mm.

IR(film): 1740 $cm^{-1}$

NMR(CDCl$_3$): 0.9(6H,d), 1.4–2.6(18H,m with bs at 1.65) δ.

MS: 220(M+), 149, 83, 135, 93, 67

EXAMPLE 8

2-isopropylidene-6,10-dimethylspiro[4.5]dec-6-en-8-ol

Reaction:

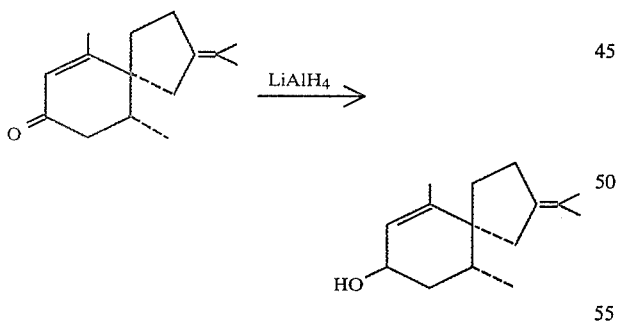

β-Vetivone (0.8 g, 0.0037 mole), prepared according to Example 4, in anhydrous ether (40 mL) was added dropwise to a stirred suspension of lithium aluminum hydride (0.07 g, 0.0018 mol) in ether (30 mL) under nitrogen. After 1 hour at room temperature, wet ether was added to destroy excess hydride and the solution was filtered through Celite. The solution was dried (Na2SO4), concentrated, and kugelrohr distilled to yield 0.64 g of the alcohol, bp 140°–145° C./0.4 mm.

IR(film): 3320, 1660 $cm^{-1}$

NMR(CDCl$_3$): 0.92(3H,bd), 1.3–2.5(19H,m), 4.18(1H,m), 5.35(1H,m) δ.

MS: 202(M-18), 134, 119, 91, 105, 159

EXAMPLE 9

A chypre type perfume composition was prepared by mixing the following:

|  | % |
|---|---|
| Oil Angelica Root | 0.5 |
| Castoreum absolute | 0.5 |
| Oil Rose | 1.0 |
| Civet absolute | 1.0 |
| Oakmoss absolute | 1.0 |
| Musk ambrette | 2.0 |
| Labdanum resinoid | 3.0 |
| Oil Ylang | 5.0 |
| Benzyl acetate | 6.0 |
| Oil Sandalwood | 7.0 |
| Vanillin | 6.0 |
| Benzyl alcohol | 9.0 |
| Jasmine extract | 12.0 |
| Coumarin | 12.0 |
| Phenylethyl alcohol | 12.0 |
| Oil Bergamot | 20.0 |
| 2-Isopropylidene-10-methylspiro[4.5]dec-6-en-8-one | 2.0 |
|  | 100.0 |

EXAMPLE 10

A perfume composition was prepared by mixing the following:

|  | % |
|---|---|
| Vanillin | 0.5 |
| Musk ketone | 4.5 |
| Coumarin | 3.0 |
| Geraniol | 3.0 |
| Oil Geranium | 1.5 |
| Benzyl acetate | 7.5 |
| Oil Cedarwood | 3.0 |
| Cedryl acetate | 9.0 |
| Hydroxycitronellal | 12.0 |
| Benzyl salicylate | 4.5 |
| Isoamyl salicylate | 4.5 |
| Oil Ylang extra | 3.0 |
| Oil Clary Sage | 1.5 |
| Oil Orange sweet Flor. | 1.5 |
| Oil Lavender Barreme | 1.5 |
| Oil Bergamot rect. | 4.5 |
| Linalool Synthetic | 3.0 |
| Linalyl acetate Synthetic | 1.5 |
| Methyl dihydrojasmonate | 3.0 |
| Oil Sandalwood, East Indian | 3.0 |
| Cinnamic alcohol ex Styrax | 0.5 |
| Phenylethyl acetate | 0.5 |
| Phenylethyl alcohol | 2.0 |
| Ionone alpha | 0.5 |
| Gamma undecalactone 10% | 0.5 |
| Rose Oxide 10% | 0.5 |
| Oil Nutmeg 10% | 0.5 |
| Oil Patchouly | 0.5 |
| Jasmin Absolute, Italian | 3.0 |
| Oil Neroli | 0.5 |
| laevo Carvone 10% | 0.5 |
| Diethyl phthalate | 9.0 |
| 2-Isopropylidene-6,10-dimethylspiro[4.5]dec-6-en-8-one | 6.0 |
|  | 100.0 |

EXAMPLE 11

A fougere type perfume composition was prepared by mixing the following:

|  | % |
|---|---|
| Coumarin | 5.0 |
| Musk ambrette | 5.0 |
| Musk aldehyde FDO | 5.0 |
| Methylionone gamma | 4.0 |
| Isoamyl salicylate | 4.0 |
| Oil Galbanum | 0.5 |
| Delta decalactone (1% in diethyl phthalate) | 0.5 |
| Santol FDO | 4.0 |
| Oil Patchouly | 6.0 |
| Oakmoss absolute incolore | 4.0 |
| Oil Neroli - Base | 7.0 |
| Oil Geranium Maroc | 10.0 |
| Phenylethyl alcohol | 3.0 |
| Oil Bergamot | 7.0 |
| Linalool synthetic | 6.0 |
| Oil Lavender 50-52% | 10.0 |
| Eugenol extra | 2.0 |
| Isoeugenol | 1.0 |
| Benzyl benzoate | 4.0 |
| 2-Isopropylidene-6,10-dimethyl-spiro[4.5]dec-6-en-8-ol | 12.0 |
|  | 100.0 |

EXAMPLE 12

A wood base was prepared by mixing the following:

|  | % |
|---|---|
| Coumarin | 4.0 |
| Olibanum resinoid | 2.0 |
| Oil Guaiacwood | 4.0 |
| Methylionone gamma | 8.0 |
| Santol FDO | 2.0 |
| Para-tertiarybutylcyclohexyl acetate | 2.0 |
| Isopropyl quinoline 10% | 4.0 |
| Oil Patchouly | 2.0 |
| Linalool synthetic | 2.0 |
| Oil Bergamot terpeneless | 4.0 |
| Oil Cedarwood | 12.0 |
| Cedryl acetate | 22.0 |
| Acetyl cedrene | 24.0 |
| 2-Isopropylidene-6,10-dimethyl-spiro[4.5]decan-8-one | 8.0 |
|  | 100.0 |

EXAMPLE 13

A floral bouquet was prepared by mixing the following:

|  | % |
|---|---|
| Musk ketone | 1.0 |
| Coumarin | 1.0 |
| Methyl everninate | 0.5 |
| Oakmoss absolute | 0.5 |
| Geraniol | 10.0 |
| Phenylethyl alcohol | 16.0 |
| Citronellol | 2.0 |
| Geranyl acetate | 1.0 |
| Indole 10% | 1.0 |
| Rose Otto | 3.0 |
| Rose oxide 10% | 1.0 |
| Hydroxycitronellal | 14.0 |
| Pentadecanolide | 1.0 |
| Methyl dihydrojasmonate | 10.0 |
| Hexyl cinnamic aldehyde | 10.0 |
| Benzyl acetate | 1.0 |
| Oil Ylang extra | 0.5 |
| Cinnamic alcohol | 0.5 |
| Phenylethyl acetate | 0.5 |

-continued

|  | % |
|---|---|
| Gamma undecalactone 10% | 0.5 |
| Cyclamen aldehyde | 0.5 |
| Ionone alpha | 0.5 |
| Methylionone gamma | 4.0 |
| Cedroxyde | 4.0 |
| Acetyl cedrene | 8.0 |
| Oil Bergamot rectified | 3.0 |
| 2-Isopropylidene-6,10-dimethyl-spiro[4.5]decan-8-one | 5.0 |
|  | 100.00 |

EXAMPLE 14

A perfume composition was prepared by mixing the following:

|  | % |
|---|---|
| Oakmoss absolute Yugoslav | 4.0 |
| Coumarin | 3.0 |
| Musk ketone | 6.0 |
| Musk ambrette | 2.0 |
| Ionone alpha | 2.0 |
| Methylionone gamma | 2.5 |
| Cinnamic alcohol | 2.5 |
| Oil Sandalwood, East Indian | 5.0 |
| Acetyl cedrene | 7.5 |
| Oil Patchouly | 1.0 |
| Amylcinnamic aldehyde | 1.0 |
| Benzyl acetate | 2.5 |
| Oil Olibanum 10% | 1.0 |
| Heliotropin | 1.0 |
| Oil Styrax | 1.0 |
| Isoeugenol | 0.5 |
| Hydroxycitronellal | 0.5 |
| Ethyl vanillin | 0.5 |
| Labdanum absolute | 0.5 |
| Oil Lemon | 1.0 |
| Oil Orange sweet Flor. | 4.0 |
| Benzyl alcohol | 2.0 |
| Phenylethyl alcohol | 2.5 |
| Phenyl acetaldehyde 10% | 1.0 |
| Rose absolute | 2.5 |
| Oil Geranium | 2.5 |
| Jasmin absolute Italian | 5.0 |
| Oil Neroli Moroccan | 0.5 |
| Aldehyde C 10 10% | 1.0 |
| Aldehyde C 11 undecylenic 10% | 4.0 |
| Aldehyde C 12 MNA 10% | 2.0 |
| Oil Bergamot rectified | 20.0 |
| 2-Isopropylidene-10-methyl-spiro[4.5]dec-6-en-8-one | 8.0 |
|  | 100.00 |

EXAMPLE 15

A lavender fragrance was prepared by mixing the following:

|  | % |
|---|---|
| Oakmoss absolute | 1.0 |
| Musk xylene | 4.0 |
| Oil Rosemary | 5.0 |
| Oil Petitgrain Paraguay | 3.0 |
| Benzyl acetate | 5.0 |
| Oil Bois de Rose | 7.0 |
| Coumarin | 10.0 |
| Terpinyl acetate | 10.0 |
| Oil Spike Lavender | 20.0 |
| Oil Lavandin | 30.0 |
| 2-Isobutylidene-10-methyl-spiro[4.5]dec-6-en-8-one | 5.0 |

EXAMPLE 16

A jasmin fragrance was prepared by mixing the following:

|  | % |
|---|---|
| Gamma undecalactone | 0.5 |
| p-Cresyl phenylacetate | 0.5 |
| Ethyl cinnamate | 0.9 |
| Oil Ylang | 7.0 |
| Geranyl acetate | 6.0 |
| Alpha amylcinnamic aldehyde | 5.0 |
| Linalool synthetic | 10.0 |
| Benzyl acetate | 20.0 |
| Phenylethyl alcohol | 20.0 |
| Hydroxycitronellal | 30.0 |
| 2-Isopropylidene-10-methyl-spiro[4.5]dec-6-en-8-one | 0.1 |
|  | 100.0 |

EXAMPLE 17

The following raspberry flavor was prepared:

|  | % |
|---|---|
| Acetic acid | 0.1 |
| Gamma undecalactone | 0.1 |
| Benzyl acetate | 0.1 |
| Oil Buchu | 0.1 |
| Maltol | 0.2 |
| 4-(p-Hydroxyphenyl)-2-butanone | 1.0 |
| Ethyl acetate | 3.0 |
| Ethyl butyrate | 1.0 |
| Hexyl acetate | 1.5 |
| Ionone beta | 0.5 |
| Irone alpha, 1% in alcohol | 0.7 |
| Hexanal | 0.8 |
| Ethyl alcohol | 90.9 |
|  | 100.00 |

This formulation was added to a tasting medium (prepared by mixing 8 oz of sugar syrup and 1 ml of a 50% aqueous solution of citric acid in 8 oz of water) at the level of 10 ppm and 2-isopropylidene-6,10-dimethyl-spiro[4.5]dec-6-en-8-ol, prepared according to Example 8, was added at a concentration of 1 ppm. The flavor which contained the spirocyclic alcohol was much preferred over a control. It added a smooth, woody character to the formulation and produced a more natural raspberry flavor.

EXAMPLE 18

An oil vetiver substitute was prepared by mixing the following:

|  | % |
|---|---|
| Oil Patchouly | 1.0 |
| Geraniol ex Palmarosa | 1.0 |
| Ionone residue | 3.0 |
| Oil Copaiba | 12.0 |
| Cedryl acetate | 13.0 |
| Oil Guaiacwood | 16.0 |
| Oil Cedarwood | 15.0 |
| Terpineol | 5.0 |
| Oil Bois de Rose | 9.0 |
| 2-Isopropylidene-6,10-dimethyl-spiro[4.5]dec-6-en-8-ol | 25.0 |
|  | 100.00 |

EXAMPLE 19

Modification of an orange flavor:

|  | % |
|---|---|
| Orange Oil Florida | 96.7 |
| 2-Isopropylidene-6,10-dimethyl-spiro[4.5]dec-6-en-8-one | 3.3 |
|  | 100.0 |

This modified orange flavor was tested at the level of 30 ppm in a beverage medium consisting of sugar, acid, and water. Whereas the straight orange oil at 30 ppm had the expected orange flavor, the modified flavor containing 2-isopropylidene-6,10-dimethylspiro[4.5]-dec-6-en-8-one ($\beta$-vetivone) (prepared according to Example 4) at the level of 1 ppm in the formulation was decidedly grapefruit in character.

EXAMPLE 20

The following cinnamon flavor compositions were prepared:

|  | A (%) | B (%) |
|---|---|---|
| Salicylic aldehyde | 0.1 | 0.1 |
| Oil Ginger | 0.3 | 0.3 |
| O-Methoxycinnamic aldehyde | 0.1 | 0.1 |
| O-Methoxybenzaldehyde | 0.5 | 0.5 |
| Methyl salicylate | 0.1 | 0.1 |
| Terpineol alpha | 2.0 | 2.0 |
| Eugenol | 2.0 | 2.0 |
| Ionone beta | 0.5 | 0.5 |
| Cinnamic aldehyde | 91.1 | 94.4 |
| 2-Isopropylidene-6,10-dimethyl-spiro[4.5]decan-8-one | 3.3 | — |
|  | 100.0 | 100.0 |

The above cinnamon flavor formulations were tasted at a level of 30 ppm. Composition A which contained 2-isopropylidene-6,10-dimethylspiro[4.5]decan-8-one (prepared according to Example 7) successfully reduced the harshness of the cinnamic aldehyde. It resuled in a softer, more natural cassia flavor.

EXAMPLE 21

The following grape base was prepared:

|  | % |
|---|---|
| Gamma undecalactone | 0.2 |
| Ionone beta | 0.8 |
| Ethyl oenanthate | 1.0 |
| Ethyl methylphenylglycidate | 1.0 |
| Cinnamic alcohol | 3.0 |
| Methylnaphthyl ketone | 3.0 |
| Methyl anthranilate | 35.0 |
| Ethyl acetate | 56.0 |
|  | 100.0 |

The above grape flavor was tasted at 30 ppm in a beverage base (sugar, water, and acid). Then 2-isopropylidene-6,10-dimethylspiro[4.5]dec-6-en-8-one (prepared according to Example 4) was added at the level of 1 ppm. The flavor developed by the grape base containing the spiroketone was much preferred. The harsh acidic taste of the base was subdued and overall resulted in a better Concord flavor.

EXAMPLE 22

2-isopropylidene-7,9-dimethylspiro[4.5]dec-6,9-dien-8-one 2,6-Dimethylphenol (2.4 g, 0.02 mol) was added to a solution of Ba(OH)$_2$.8H$_2$O (6.6 g, 0.021 mol) in distilled water (12 mL). The mixture was cooled to 15° C. and 2-isopropylidene-1,4-dichlorobutane (3.6 g, 0.022 mol) was added over 1 hour under nitrogen. Stirring at room temperature was continued for 5 hours and then the reaction mixture was extracted with ether. The ether extracts were washed with 10% sodium hydroxide, water, and dried (Na$_2$SO$_4$). Concentration gave 4.7 g of crude material which was mainly the alkylated phenol having the structure:

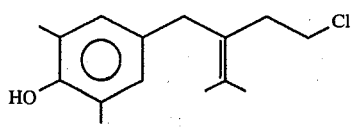

A sample purified by preparative glc had the following spectral characteristics:

IR(film): 3600, 3450 cm$^{-1}$

NMR(CDCl$_3$): 1.8(6H,s), 2.2(6H,s), 2.45(2H,m), 3.38(4H,m), 4.45(1H,s), 6.75(2Hs) δ.

MS: 252 and 254 (M+), 135, 189, 122, 91, 41

The crude alkylated phenol (4.5 g) was added dropwise to a solution of potassium t-butoxide (2.8 g, 0.025 mol) in t-butanol (800 mL) under nitrogen. The reaction mixture was refluxed for 5 hours. Most of the t-butanol was then removed on a rotary evaporator and the residue partitioned between ether and water. The ether extract was washed several times with water and dried (Na$_2$SO$_4$). Kugelrohr distillation afforded 3.1 g, bp 130° C./0.5 mm, of spirodienone having the structure:

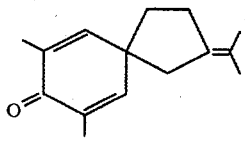

IR(film): 1670, 1640 cm$^{-1}$

NMR(CDCl$_3$): 1.65(6H,bs), 1.8-2.75(12H, m with s at 1.86), 6.65(2,H,bs) δ.

MS: 216(M+), 201, 135, 173, 91, 145

EXAMPLE 23

2-isopropylidene-7,9-dimethylspiro[4.5]decan-8-one

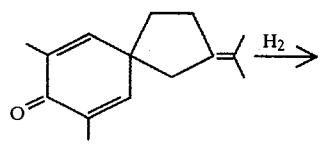

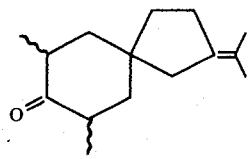

A solution of 2-isopropylidene-7,9-dimethyl-spiro[4.5]-dec-6,9-dien-8-one (3 g, 0.014 mol), prepared according to Example 22, in hexane (120 mL) was hydrogenated at room temperature and 1 atmosphere over 5% palladium on carbon (0.2 g). After uptake of two equivalents of hydrogen was complete, the solution was filtered through celite and concentrated. Short path distillation gave 2.6 g of the ketone, bp 80°-85° C./0.05 mm, as a mixture of isomers (glc/ms).

IR(film): 1720 cm$^{-1}$

NMR(CDCl$_3$): 0.95(6H, overlapping doublet), 1.2-2.8(18H, m with bs at 1.62) δ.

MS(major isomer): 220(M+), 205, 67, 83, 97, 121

EXAMPLE 24

2-isopropylidene-7,9-dimethylspiro[4.5]decan-8-ol

To a suspension of lithium aluminum hydride (0.19 g, 5 mmol) in anhydrous ether (10 mL) was added 2-isopropylidene-7,9-dimethylspiro[4.5]decan-8-one (1.6 g, 7.3 mmol), prepared according to Example 23, in ether (3 mL) under nitrogen. The mixture was stirred at room temperature for 2 hours and then excess hydride decomposed by addition of wet ether. The solution was filtered, dried (Na$_2$SO$_4$) and concentrated on a rotary evaporator. Kugelrohr distillation gave 1.4 g, bp 150° C./0.5 mm, of the alcohol having the structure:

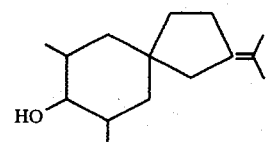

IR(film): 3375 cm$^{-1}$

NMR(CDCl$_3$): 0.95(6H,m), 1.1-2.5(19H, m with bs at 1.6), 3.5(1H,m) δ.

MS(major isomer): 222(M+), 149, 107, 207, 148, 119

EXAMPLE 25

2-isopropylidene-7,9-dimethyl-8-methoxyspiro[4.5]decane

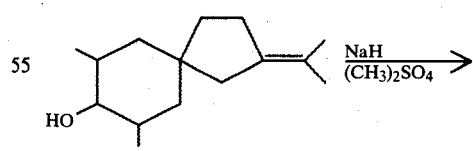

A suspension of sodium hydride (5 mmol) in anhydrous dimethylformamide (5 mL) was warmed to 50° C. under N$_2$. 2-Isopropylidene-7,9-dimethylspiro[4.5]decan-8-ol (0.9 g, 4 mmol), prepared according to Example 24, was added dropwise and heating continued for an additional 1.5 hours. Dimethyl sulfate (0.5 g, 4 mmol) was added and the temperature was maintained at 50°–55° C. for 1 hour. The solution was poured into water and extracted with ether followed by drying (Na₂SO₄) and solvent removal on a rotary evaporator. Kugelrohr distillation gave 0.71 g, bp 110° C./0.5 mm, of the ether as a mixture of isomers (glc/ms).

IR(film): 1108 cm$^{-1}$

NMR(CDCl₃): 0.6–2.4 (24H, complex pattern), 3.45(4H, m with superimposed s)

MS(major isomer): 236 (M+), 121, 148, 149, 107, 93

EXAMPLE 26

2-isopropylidene-6,9-dimethylspiro[4.5]dec-6,9-dien-8-one 2,5-Dimethylphenol (9.7 g, 0.08 mol) was added to a solution of sodium hydroxide (3.2 g, 0.08 mol) and sodium acetate (3.3 g, 0.04 mol) in distilled water (50 mL). The mixture was cooled to 15° C. and 2-isopropylidene-1,4-dichlorobutane (15 g, 0.09 mol) was added over 1 hour under nitrogen. After stirring at room temperature for 6 hours, the reaction mixture was extracted with ether. The ether extracts were washed with 10% sodium hydroxide, water, and dried (Na₂SO₄). Concentration gave 18.5 g of crude material consisting of mainly the alkylated phenol having the structure:

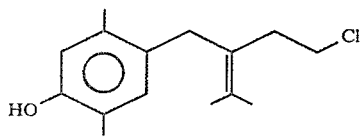

A sample purified by column chromatography (silica gel) had the following spectral characteristics:
IR(film): 3450 cm$^{-1}$ NMR(CDCl₃): 1.7(6H,2s), 2.15(6H,s), 2.42(2H,bt), 3.3(4H,m), 4.8(1H,s), 6.55(1H,s), 6.75(1H,s) δ.

MS: 252 and 254 (M+), 135, 201, 216, 173, 91

The crude material was mixed with powdered sodium hydroxide (3.2 g) and the mixture heated under a vacuum of 1 mm. Distillate boiling over the range of 120°–135° C. was collected and chromatographed on deactivated silica gel (150 g) eluting with hexane-ethyl acetate 85:15 to yield 5.4 g of the spirodienone having the structure:

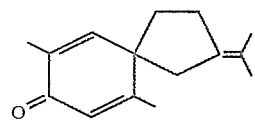

which was crystallized from petroleum ether, mp 52°–63° C.

IR(CHCl₃) 1660 cm$^{-1}$

NMR(CDCl₃): 1.4–2.8(18H, complex pattern with broad singlet at 1.65 and doublets at 1.9 and 2.0), 5.15(1H,m), 6.7(1H,m) δ.

MS: 216 (M+), 201, 122, 173, 135, 91

EXAMPLE 27

2-isopropylidene-6,9-dimethylspiro[4.5]decan-8-one

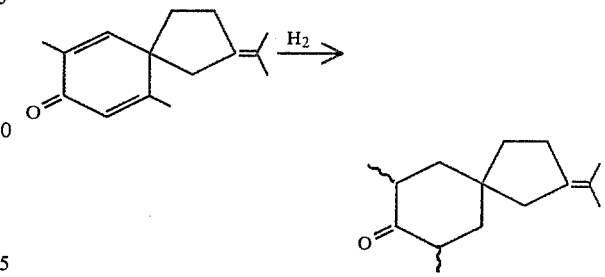

A solution of 2-isopropylidene-6,9-dimethylspiro[4.5]-dec-6,9-dien-8-one (2.16 g, 0.01 mol), prepared according to Example 26, in hexane (75 mL) was hydrogenated at room temperature and 1 atmosphere over 5% palladium on carbon (0.4 g). After uptake of 2 equivalents of hydrogen, the solution was filtered through celite and concentrated. The crude product was kugelrohr distilled to give 2.0 g of the ketone, bp 130° C./0.5 mm, as a mixture of isomers (glc/ms).

IR(film): 1720 cm$^{-1}$

NMR(CDCl₃): 0.9 (6H,m), 1.3–2.45(18H,m)δ.

MS(major isomer): 220 (M+), 149, 83, 148, 107, 93

EXAMPLE 28

A fougere type perfume composition was prepared by mixing the following:

|  | % |
|---|---|
| Coumarin | 3.0 |
| Musk ketone | 4.0 |
| Musk ambrette | 6.0 |
| Isoamyl salicylate | 8.0 |
| Vanillin from lignin | 2.0 |
| Oil Geranium Maroc | 3.0 |
| Oil Patchouly | 3.0 |
| Phenylethyl alcohol | 3.0 |
| Geraniol | 6.0 |
| Oil Bergamot | 10.0 |
| Heliotropin | 3.0 |
| Oakmoss absolute incolore | 2.0 |
| Anisic aldehyde | 1.0 |
| Santol FDO | 2.0 |
| Oil Lavender 50–52% | 8.0 |
| Linalool synthetic | 7.0 |
| Eugenol extra | 2.0 |
| Oil Lemon Italian | 10.0 |
| Lilial | 6.0 |
| Benzyl benzoate | 8.0 |
| 2-Isopropylidene-7,9-dimethyl-spiro[4.5]-decan-8-one | 3.0 |
|  | 100.0 |

EXAMPLE 29

A chypre type fragrance composition was prepared by mixing the following:

|  | % |
|---|---|
| Oil Angelica Root | 0.5 |
| Castoreum absolute | 0.5 |
| Oil Rose | 1.0 |
| Civet absolute | 1.0 |
| Oakmoss absolute | 1.0 |
| Musk ambrette | 2.0 |
| Labdanum resinoid | 3.0 |
| Oil Ylang | 5.0 |

-continued

|  | % |
|---|---|
| Benzyl acetate | 6.0 |
| Oil Sandalwood | 7.0 |
| Vanillin | 6.0 |
| Benzyl alcohol | 9.0 |
| Jasmine extract | 12.0 |
| Coumarin | 12.0 |
| Phenylethyl alcohol | 12.0 |
| Oil Bergamot | 20.0 |
| 2-Isopropylidene-6,9-dimethyl-spiro[4.5]decan-8-one | 2.0 |
|  | 100.0 |

EXAMPLE 30

A violet perfume composition was prepared by mixing the following:

|  | % |
|---|---|
| Musk ambrette | 0.6 |
| Jasmin absolute | 0.3 |
| Violet leaves absolute | 0.1 |
| Heliotropin | 1.0 |
| Methylionone | 3.0 |
| Benzoin Siam | 2.0 |
| Oil Cedarwood | 20.0 |
| Oil Sandalwood | 30.0 |
| Oil Orris Root | 40.0 |
| 2-Isopropylidene-7,9-dimethyl-sprio[4.5]-decan-8-one | 3.0 |
|  | 100.00 |

EXAMPLE 31

A fougere type perfume composition was prepared by mixing the following:

|  | % |
|---|---|
| Undecyclenic aldehyde | 0.2 |
| Civet absolute | 0.3 |
| Vanillin | 0.5 |
| Rose Otto | 0.5 |
| Acetophenone | 0.5 |
| Anisic aldehyde | 1.0 |
| Oil Clary Sage | 1.0 |
| Isoamyl salicylate | 2.0 |
| Oil Patchouly | 2.0 |
| Jasmin absolute | 3.0 |
| Oil sandalwood | 3.0 |
| Linalool synthetic | 4.0 |
| Coumarin | 7.0 |
| Benzyl acetate | 10.0 |
| Oil Bois de Rose | 10.0 |
| Oil Lavender | 20.0 |
| Oil Bergamot rectified | 30.0 |
| 2-Isopropylidene-7,9-dimethyl-8-methoxyspiro[4.5]decane | 5.0 |
|  | 100.0 |

EXAMPLE 32 tobacco flavor composition

A 1% ethanol solution of 2-isopropylidene-6,10-dimethylspiro[4.5]dec-6-en-8-one was sprayed on smoking tobacco in an amount sufficient to provide a tobacco composition containing 70 ppm of the flavor additive on a dry basis.

To produce a flavored tobacco which also contained synthetic tobacco, the procedure for the production of a tobacco flavor composition heretofore described in this Example was repeated except that a synthetic tobacco such as cellulose fibers, for example, "CYTREL" (a trademark of the Celenese Chemical Corporation) or "POLYSTREP" (a trademark of the Imperial Chemical Corporation) was mixed with the tobacco in a ratio of approximately 1 to 1 by weight.

In a third procedure, a 1% ethanol solution of 2-isopropylidene-6,10-dimethylspiro[4.5]dec-6-en-8-one was sprayed onto synthetic tobacco at the level of 70 ppm on a dry weight basis.

Tobacco flavor compositions prepared by any one of the above methods may then be used in the manufacture of cigarettes.

In a panel evaluation against control cigarettes, the taste of the flavored cigarettes was described as "fresh" and "woody" in character.

EXAMPLE 33 tobacco flavor composition

A 1% ethanol solution of 2-isopropylidene-10-methylspiro[4.5]dec-6-en-8-one was employed at the level of 60 ppm in a similar manner to that described in Example 32.

The taste, as evaluated in cigarettes, was described as possessing a floral and woody character.

EXAMPLE 34 tobacco flavor composition

By replacing the ketone in Example 32 with 2-isopropylidene-7,9-diemthylspiro[4.5]decan-8-one at the level of 30 ppm, the taste had a strong, cedar character.

As will be obvious to one skilled in the art, many modifications, variations and alterations are possible in the practices of this invention without departing from the spirit and scope thereof. For example, many of the intermediates disclosed may be useful in and of themselves as flavor and/or fragrance modifying substances.

What is claimed is:

1. A process for preparing a spiroketone having the structure:

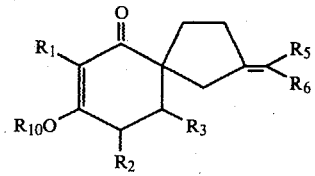

wherein each of $R_1$, $R_2$, $R_3$, $R_5$, and $R_6$ may be hydrogen or lower alkyl, and wherein $R_{10}$ is lower alkyl which comprises:

(a) reacting a substituted cyclohexanone carboxylate having the structure:

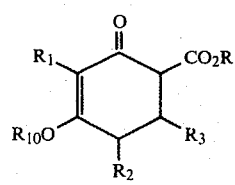

wherein R may be methyl or ethyl, with an alkylidene 1,4-dihalobutane having the structure:

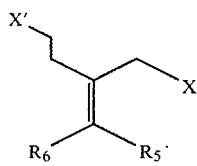

wherein each of X and X' may be chloro, bromo, or iodo, in the presence of a base such as an alkali metal hydride to form a carboxylate compound having the structure:

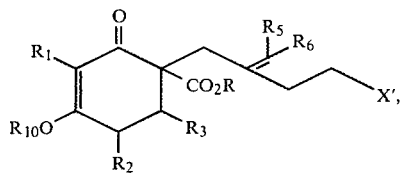

said reaction being carried out in a suitable solvent and at a suitable temperature in the range from about 0° to about 150° C. and said base being present in an amount equal to about one equivalent; and (b) decarboxylatively alkylating the compound formed in the presence of an alkali metal salt in a polar aprotic solvent to produce said spiroketone, said decarboxylative alkylation being carried out at a temperature in the range from about 80° to about 160° C. and the mole ratio of said carboxylate compound to said alkali metal salt being in the range from about 1:0.5 to 1:10.

2. A process in accordance with claim 1 wherein the alkylation reaction of step (a) is additionally carried out in the presence of a phase transfer agent having the formula:

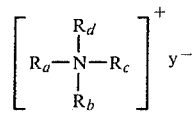

wherein at least one of $R_a$, $R_b$, $R_c$ and $R_d$ is $C_6$–$C_{10}$ aryl, $C_6$–$C_{11}$ aralkyl, $C_8$–$C_{22}$ alkyl, or $C_8$–$C_{22}$ alkenyl, the remainder are $C_1$–$C_5$ alkyl and $Y^-$ is a halogen or hydroxyl anion, the amount of said phase transfer agent relative to the amount of said substituted cyclohexanone carboxylate being in the range from about 0.1 to 10.0 mole percent.

3. A process in accordance with claim 1 wherein said substituted cyclohexanone carboxylate is methyl-2-oxo-4-isopropoxy-6-methyl-3-cyclohexene carboxylate.

4. A process in accordance with claim 1 wherein said alkylidene-1,4-dihalobutane is 2-isopropylidene-1,4-dichlorobutane.

5. A process in accordance with claim 1 wherein said base is sodium hydride.

6. A process in accordance with claim 1 wherein said alkali metal salt is lithium chloride.

* * * * *

UNITED STATES PATENT AND TRADEMARK OFFICE
CERTIFICATE OF CORRECTION

PATENT NO. : 4,281,204
DATED : July 28, 1981
INVENTOR(S) : BRIAN J. WILLIS ET AL It is certified that error appears in the above-identified patent and that said Letters Patent are hereby corrected as shown below:

COL. 4, line 9, "5,6-ethylcyclohexane" should read
-- 5,6-diethylcyclohexane --

COL. 5, correct the formula under Scheme A to read:

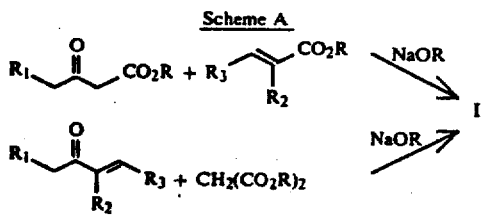

Signed and Sealed this

Sixteenth Day of February 1982

[SEAL]

Attest:

GERALD J. MOSSINGHOFF

Attesting Officer

Commissioner of Patents and Trademarks